United States Patent [19]
Djuric et al.

[11] Patent Number: 5,380,740
[45] Date of Patent: Jan. 10, 1995

[54] ANTI-INFLAMMATORY COMPOUNDS, COMPOSITIONS AND METHOD OF USE THEREOF

[75] Inventors: Stevan W. Djuric, Glenview; Donald J. Fretland, Highland; Stella S. Yu, Morton Grove, all of Ill.

[73] Assignee: G. D. Searle & Co., Chicago, Ill.

[21] Appl. No.: 50,109

[22] Filed: Apr. 28, 1993

[51] Int. Cl.$^6$ .............. C07D 311/66; C07D 405/13; A61K 31/35; A61K 31/41
[52] U.S. Cl. ............................ 514/382; 514/451; 548/252; 549/408
[58] Field of Search ............... 548/253; 514/382, 451; 549/408

[56] References Cited

U.S. PATENT DOCUMENTS

| | | | |
|---|---|---|---|
| 3,882,148 | 5/1975 | Augstein et al. | 260/345.2 |
| 4,281,008 | 7/1981 | Chamberlain et al. | 424/269 |
| 4,546,194 | 10/1985 | Miyano et al. | 549/399 |
| 4,565,882 | 1/1986 | Miyano et al. | 549/401 |
| 4,665,203 | 5/1987 | Miyano et al. | 549/402 |
| 4,778,903 | 10/1988 | Miyano et al. | 549/407 |
| 4,889,871 | 12/1989 | Djuric et al. | 514/456 |

FOREIGN PATENT DOCUMENTS

| | | | |
|---|---|---|---|
| 80300565.1 | 10/1980 | European Pat. Off. | C07D 311/22 |
| 84107289.5 | 1/1985 | European Pat. Off. | C07D 311/58 |
| 0150447 | 7/1985 | European Pat. Off. | C07D 311/66 |
| 82201368.6 | 5/1987 | European Pat. Off. | C07D 311/24 |
| 62-8432 | 2/1987 | Japan | C07D 311/22 |

OTHER PUBLICATIONS

R. Appleton, et al. "Antagonists of Slow Reacting Substance of etc.", J. Med. Chem. 20(3), 371-379 (1977).
N. Cohen, et al. "3,4-Dihydro-2H-1-benzopyran-2-carboxylic acids and related compounds as leudotriene antagonists", Chemical Abstracts, vol. 111, No. 17, p. 697, abstract No. 153565y (1989).
N. Cohen, et al. "3,4-Dihydro-2H-1-bensopyran-2-carboxylic acids and related compounds as leudotriene antagonists", J. Med. Chem. 32(8), 1842-60 (1989).
S. Djuric, et al. "Continuous method for production of 2-aldoxy-3,4-dihydropans", Chemical Abstracts, vol. 110, No. 25, p. 620, abstract No. 231387n, (Jun. 1989).
S. Djuric, et al. "7-[3-(4-Acetyl-3-methoxy-2-propylphenoxy)propoxyl]-3,4-dihydro-8-propyl-2H-1-benzopyran-2-carboxylic Acid: An Orally Active Selective Leukotriene B$_4$ Receptor Antagonist", J. Med. Chem. 32(6), 1145-7 (Jun. 1989).
G. D. Searle & Co. "Benzopyran antimetabolites", Chemical Abstracts, vol. 103, No. 19, p. 699, abstract No. 160389g (Nov. 1985).

*Primary Examiner*—David B. Springer
*Attorney, Agent, or Firm*—Scott B. Feder; Roger A. Williams

[57] ABSTRACT

This invention encompasses compounds of the following formula and the stereoisomers and pharmaceutically acceptable salts thereof.

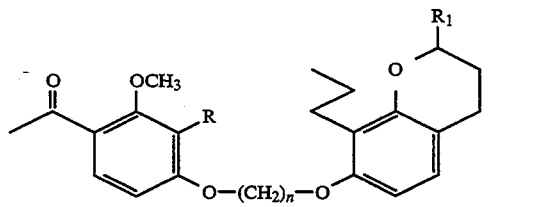

wherein R represents lower alkyl of 1 to 6 carbon atoms, lower alkenyl of 2 to 6 carbon atoms, or —(CH$_2$)$_m$—R$^3$ wherein R$^3$ represents cycloalkyl of 3 to 5 carbon atoms and m is 1, 2 or 3; R$_1$ is —CONH$_2$ or

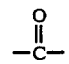

NHSO$_2$R$_2$ wherein R$_2$ is lower alkyl, phenyl, unsubstituted or substituted with loweralkyl, or

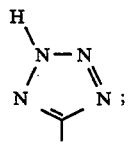
and n is an integer from 2 to 5. The compounds are useful anti-inflammatory agents for treating, for example, inflammatory bowel disease, rheumatoid arthritis, gout, asthma and psoriasis.
29 Claims, No Drawings

ANTI-INFLAMMATORY COMPOUNDS, COMPOSITIONS AND METHOD OF USE THEREOF

BACKGROUND OF THE INVENTION

Leukotriene $D_4$ and $C_4$ ($LTD_4$/$LTC_4$) and leukotriene $B_4$ ($LTB_4$) are products of the arachidonic acid metabolic pathway. $LTD_4$ and $LTC_4$ are associated with smooth muscle contraction and contract guinea pig ileum, human and guinea pig bronchi and human pulmonary artery and vein. $LTB_4$ is associated with neutrophil stimulation and is characterized by chemotaxis, aggregation and degranulation. $LTB_4$ is believed to be an important mediator of inflammation. High levels of $LTB_4$ are detected in rheumatoid arthritis, gout, psoriasis, and inflammatory bowel disease. Thus antagonists of $LTB_4$ are useful in the therapy of such diseases.

Gastroenterology, 1985: 88:580-7 discusses the role of arachidonic acid metabolites in inflammatory bowel disease.

British Medical Bulletin, (1983), vol. 39, No. 3, pp. 249-254, generally discusses the pharmacology and pathophysiology of leukotriene B4.

Biochemical and Biophysical Research Communications, Vol. 138, No. 2 (1986), pp. 540-546 discusses the pharmacology of a specific $LTB_4$ antagonist which has a different structure than compounds of this invention.

The Journal of Medicinal Chemistry, 1977, Vol. 20 (3): 376 discloses a compound similar to the compounds of Formula I.

The prior art generally describes the above compounds as $LTD_4$ antagonists for use as anti-allergy compounds or as antagonists of SRS-A, the slow reacting substance of anaphylaxis. In sharp contrast, compounds of Formula I are selective $LTB_4$ antagonists useful treating inflammatory diseases.

U.S. Pat. Nos. 4,281,008, 3,822,148, and 4,006,245 generically disclose formulae which encompass compounds similar to Formula I but do not exemplify or otherwise enable the preparation and use of such compounds, nor do they teach the selective $LTB_4$ antagonist activity of compounds of the present invention.

U.S. Pat. No. 4,889,871 generically discloses formulae which encompass the compound 1 described in Scheme 1 herein and which is used as an intermediate in the preparation of the compounds of this invention. The compounds are disclosed as useful anti-inflammatory agents.

SUMMARY OF THE INVENTION

This invention encompasses compounds of the following formula and the stereoisomers and pharmaceutically acceptable salts thereof.

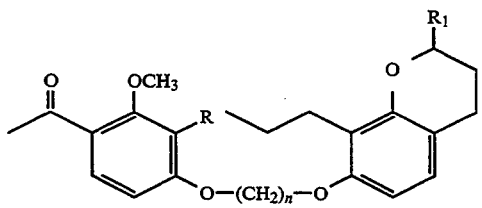

wherein

R represents lower alkyl of 1 to 6 carbon atoms, lower alkenyl of 2 to 6 carbon atoms, or —(CH$_2$)$_m$—R$^3$ wherein R$^3$ represents cycloalkyl of 3 to 5 carbon atoms and m is 1, 2 or 3; R$_1$ is —CONH$_2$ or

NHSO$_2$R$_2$ wherein R$_2$ is lower alkyl, phenyl, unsubstituted or substituted with lower alkyl, or

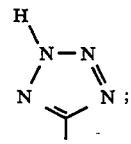

and n is an integer from 2 to 5.

These compounds are selective antagonists of leukotriene $B_4$ ($LTB_4$) with little or no antagonism of leukotriene $D_4$ ($LTD_4$) and are useful anti-inflammatory agents for treating inflammatory bowel disease, rheumatoid arthritis, gout, asthma and psoriasis.

DETAILED DESCRIPTION OF THE INVENTION

This invention encompasses the compounds of Formula I as previously described.

Preferred embodiments of the present invention are compounds of the Formula Ia, and the stereoisomers and pharmaceuticallF acceptable salts thereof,

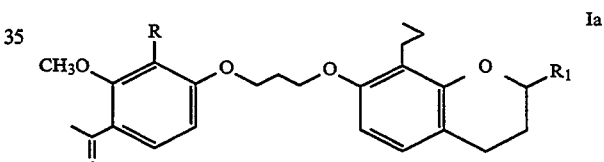

wherein R is propyl, 2-propenyl or cyclopropylmethyl, and R$_1$ is

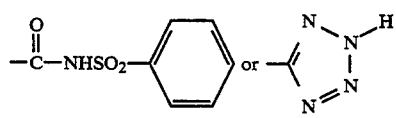

It is implicit in this application that the tetrazole moiety consists of the tautomeric structures

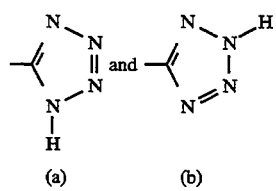

(a)      (b)

with (b) being used herein to depict the tetrazole moiety.

Pharmaceutically acceptable salts such as ammonium, sodium, potassium, alkaline earth, tetraalkylammonium and the like are encompassed by the invention.

Scheme 1 illustrates a specific embodiment of the method for preparing compounds of the invention.

SCHEME 1

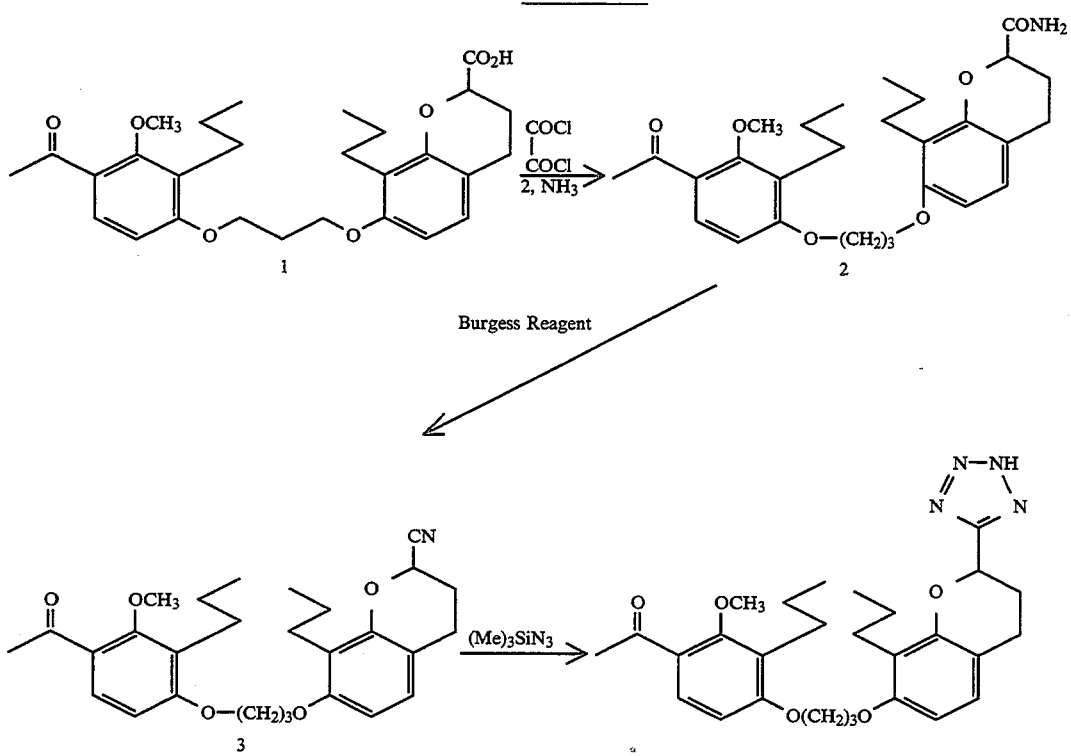

EXAMPLE 1

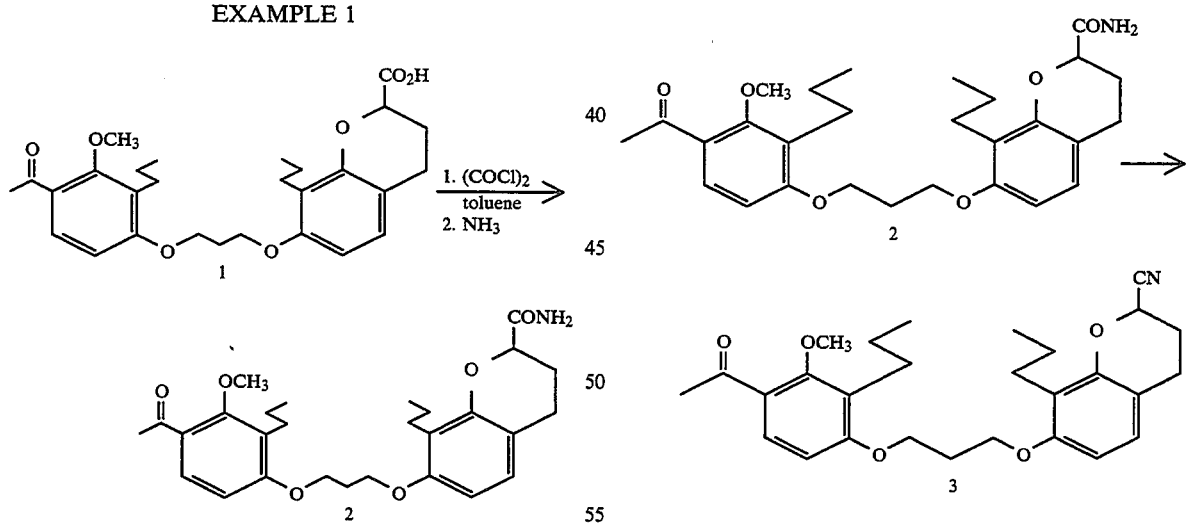

Referring to Scheme 1, 2.1 grams of compound 1 were dissolved in 50 ml. of toluene and 15 ml. of $(COCl)_2$ was added. The mixture was stirred at room temperature for four hours. The reaction was then stopped, the solvent was removed in vacuo to produce a crude oil and 150 ml. of $CH_2Cl_2$ was added. The solution was then cooled to room temperature and $NH_3$ gas was bubbled through the solution for one hour. The reaction mixture was then poured into 150 ml of water, the layers were separated and the aqueous layer was extracted three times with $CH_2Cl_2$. The mixture was then filtered and dried to obtain 1.45 grams of compound 2.

EXAMPLE 2

1.35 (2.79 m mole) grams of compound 2 were dissolved in 15 ml of $CH_2Cl_2$ and 2.50 grams (9.77 m mole) of Burgess reagent* were added. The mixture was stirred at room temperature overnight and stripped of solvent to obtain 1.30 grams of compound 3.

*Burgess, Reagent $CH_3O_2CNSO_2NEt_3$ methyl(carboxysulfamoyl)triethylammonium hydroxide inner salt. J. Org. Chem. 38 26 (1973)

| Elements | Calculated | Found |
|---|---|---|
| Carbon | 72.23 | 72.23 |
| Hydrogen | 7.58 | 7.62 |
| Nitrogen | 3.01 | 3.03 |

EXAMPLE 3

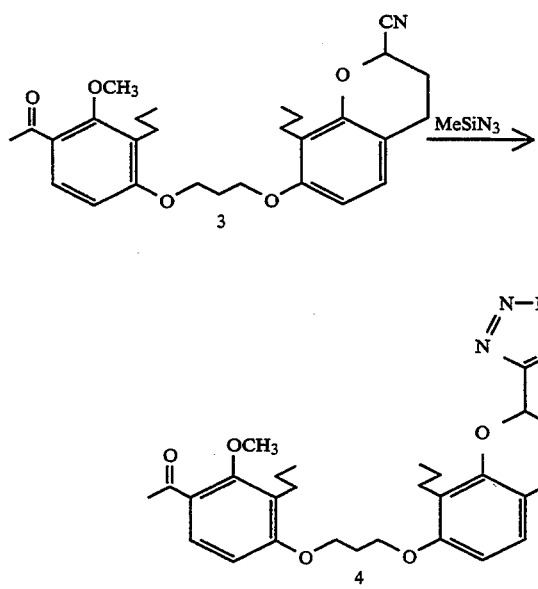

958.2 mg of compound 3 and 203.4 mg. of $(CH_3)_3 Si N_3$ were placed in a 4C ml reaction vial which was sealed and heated to 150° C. overnight. The heating was continued for an additional 44 hours for a total heating time of 64 hours. The reaction mixture was then passed through a silica column with a 5/95/1 mixture of $CH_3OH/CH_2Cl_2$/acetic acid. 100 mg of the product, compound 4, was obtained.

| Elements | Calculated | Found |
|---|---|---|
| Carbon | 66.12 | 66.23 |
| Hydrogen | 7.13 | 7.15 |
| Nitrogen | 11.02 | 10.95 |

EXAMPLE 4

Synthesis of Sulfonamides

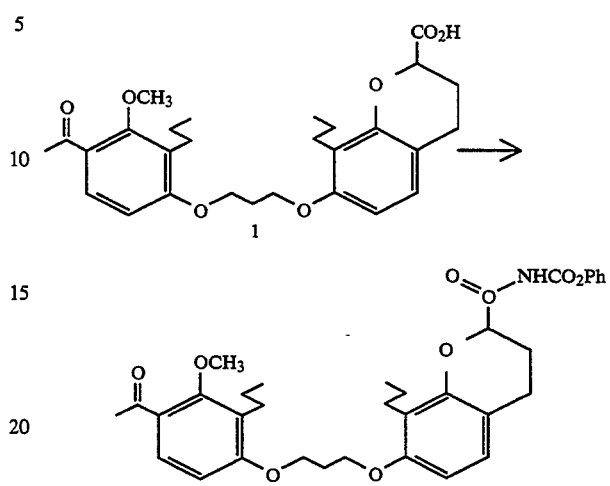

A mixture of 2.9 g (6 mMol) of compound 1, 0.96 g benzenesulfonamide, 0.96 g (7.8 mMol) of 4-(dimethylamino)pyridine, 1.08 g (6 mMol) of 1-[3-(dimethylamino)propyl]-3-ethylcarbodiimide hydrochloride, 5 g of 4A molecular sieves and 60 mL of dry dichloromethane was stirred at room temperature for 4 days. The reaction mixture was filtered and the filtrate was washed with 1N HCl, water and brine. Evaporation of the dry ($Na_2SO_4$) solvent in vacuo afforded crude product which was purified by chromatography on silica gel (hexane/ethyl acetate/acetic acid, 65/34/1 as eluant) to afford 3.1 g of product.

Microanalysis: Theory C 65.47, H 6.62, N 2.25
Found: C 65.18, H 6.67, N 2.25

EXAMPLE 5

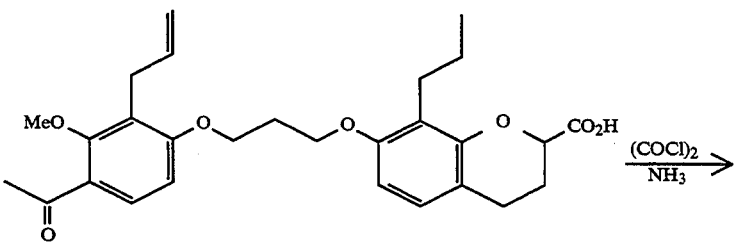

A

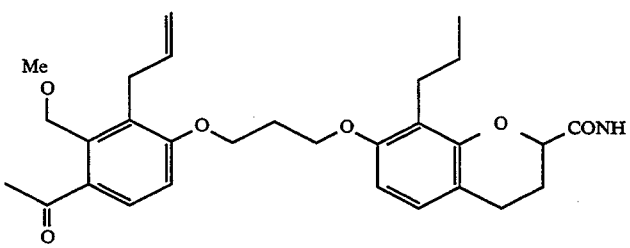

B

Compound A (2.1 g) was dissolved in dry toluene and oxalyl chloride (1.2 equivalents) added with stirring under argon. 1 drop of DMF was added and the reaction mixture was stirred at room temperature for 1 hour.

The solvent was removed in vacuo and the residue dissolved in dry CH$_2$Cl$_2$ and ammonia gas slowly bubbled through the solution for 20 minutes. Water (100 cm$^3$) was added and the organic layer separated, dried over magnesium sulfate and the volatiles removed in vacuo. The resulting residue was purified by silica gel chromatography to afford compound (B) as a white solid (1.8 g).

Analysis: Calculated for C$_{28}$H$_{35}$NO$_6$ C 69.83, H 7.32, N 2.91 Found: C 69.60, H 7.23, N 2.86

EXAMPLE 6

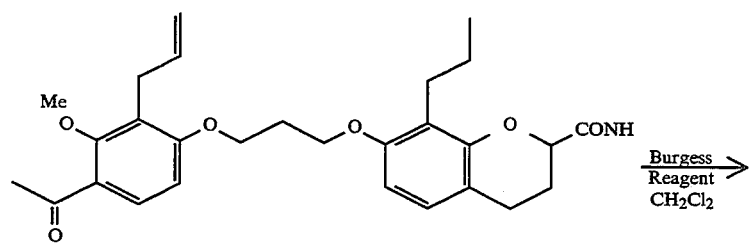

B 3.0 g of compound B were dissolved in methylene chloride (25 cm$^3$) containing Burgess reagent (4.0 g) and the mixture stirred at room temperature overnight. At this point, the solvent was removed and the residue purified by chromatography on silica gel using ethyl acetate/hexane (2:8) as eluant. Compound (C) was isolated as a colorless oil (2.8 g).

EXAMPLE 7

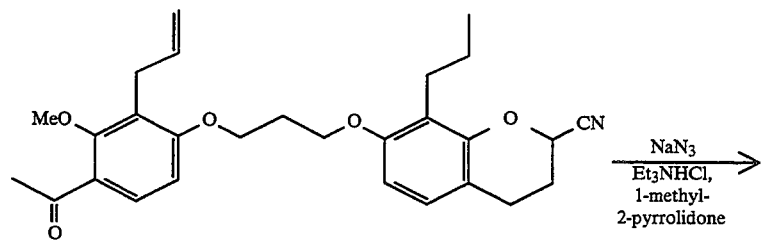

C

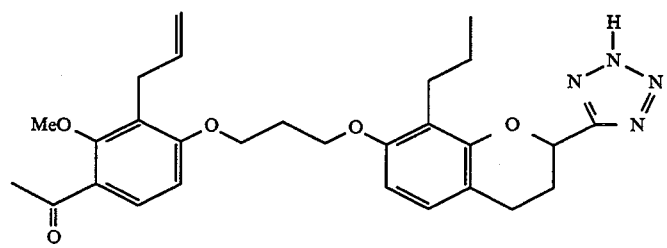

D

Compound (C) (2.8 g), sodium azide (1.2 g) and triethylamine hydrochloride (1.2 g) were dissolved in 1-methyl 2-pyrrolidone (60 cm$^3$) and the solution heated at 150° C. for 2 hours. The mixture was poured into 200 cm$^3$ of water, acidified with dilute HCl and then extracted with ethyl acetate. The organic layers were dried and evaporated in vacuo to afford a crude residue which was purified by chromatography on silica gel using ethyl acetate/hexane/acetic acid (50:49:1) as solvent. Compound (D) was obtained as a white solid (2.1 g).

Analysis for C$_{28}$H$_{34}$N$_4$O$_5$ Calculated: C 66.39, H 6.76, N 11.06 Found: C 66.19, H 6.87, N 11.26

EXAMPLE 8

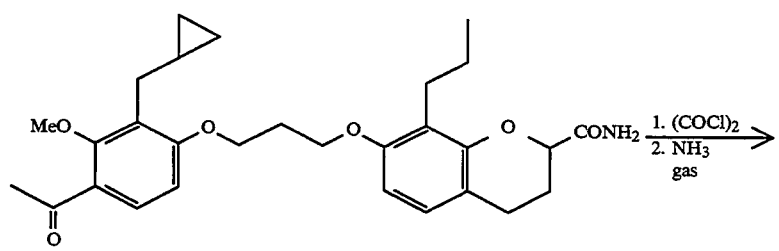
E
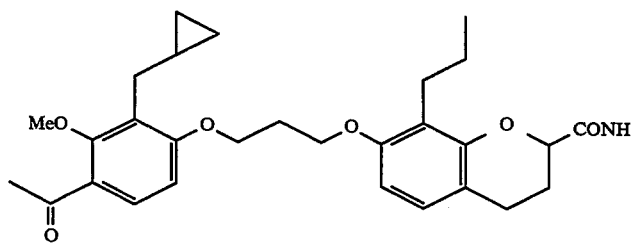
F
Compound (E), (1.0 g) was converted to the amide, compound, (F) as illustrated in Example 5. 1.0 g of compound (F) was obtained after chromatography of the crude product on silica gel using ethyl acetate/hexane (3:7) as eluant.
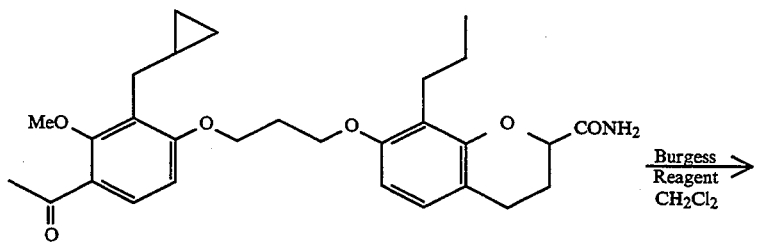
F
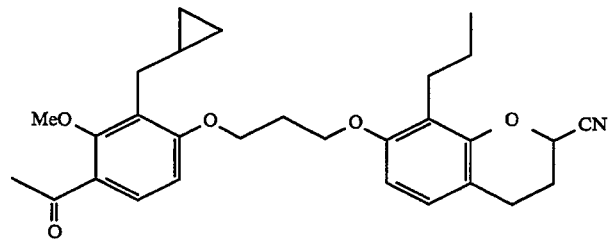
G
EXAMPLE 9
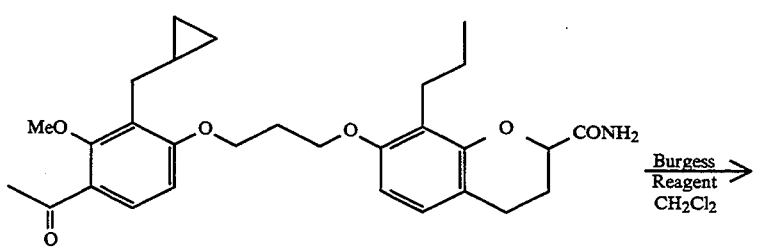
F -continued

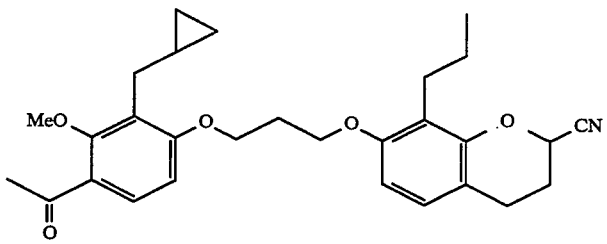

G

Compound F, (1.0 g) was treated with Burgess reagent under the conditions described in Example 6. The crude product thus obtained was purified by chromatography on silica gel using hexane/ethyl acetate (2:8) as eluant. Compound G (870 mgs) was isolated as a colorless oil.

Micro Analysis for $C_{29}H_{35}NO_5$ Calculated: C 72.93, H 7.39, N 2.93 Found: C 72.45, H 7.30, N 2.90

EXAMPLE 10

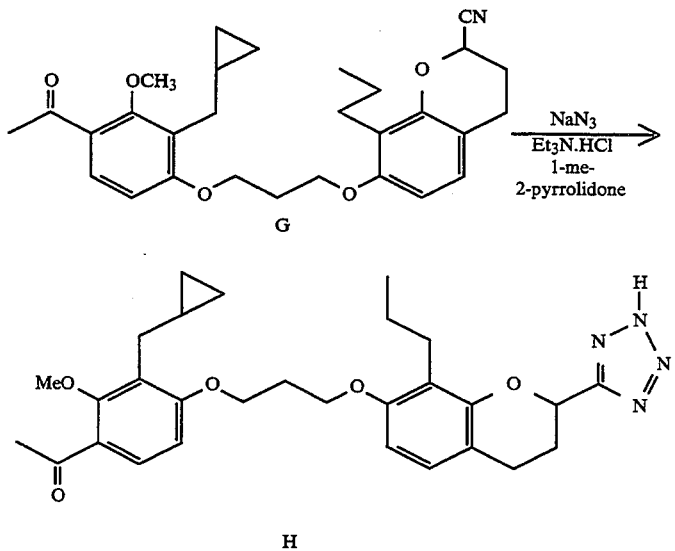

Compound G (0.8 g) was converted to the tetrazole H by treatment with sodium azide (330 mgs), triethylamine hydrochloride (0.3 g) in 1-methyl 2-pyrrolidone (20 cm$^3$). The mixture was heated at 150° C. for 2 hours and then partitioned between 2N HCl and ethyl acetate. The organic layer was removed, dried (MgSO$_4$) and stripped in vacuo to afford a crude oil. This material was purified by chromatography on silica gel (ethyl acetate/hexane/acetic acid (50:49:1) as eluent) to provide 720 mgs. of compound H.

Micro Analysis for $C_{29}H_{36}N_4O_5$ Calculated: C 66.90, H 6.97, N 10.76 Found: C 66.54, H 6.93, N 10.88

The biological activity of the compounds of this invention was determined by the following test procedures.

Preparation of Human Neutrophils

Neutrophils were purified from venous blood of normal human donors using standard techniques of dextran sedimentation, centrifugation on Ficoll-paque ® (Pharmacia) or Histopaque ® sterile solution (Sigma) and hypotonic lysis of erythrocytes (Boyum, A., *Isolation of Leukocytes from Human Blood: Further Observations. Stand, J. Lab. Clin. Invest.*, 21 (Suppl. 97): 31, 1968). The purity of isolated neutrophils was >95%.

Human Neutrophil Degranulation Assay

Neutrophil degranulation was determined by measuring the release of myeloperoxidase activity into the incubation medium. Neutrophils (3×10$^6$) in 1 ml HBSS solution were preincubated with cytochalasin B(5 μg) at 37° C. for 5 minutes, followed by preincubation with test compounds for 7 minutes. Neutrophils were then incubated for 2 to 20 minutes with LTB$_4$(5×10$^{-8}$M) to induce degranulation. Following incubation, samples were centrifuged and myeloperoxidase was extracted from the cell pellets by sonication in phosphate buffer containing 0.4% Triton X-100. Triton X-100 was also added to the supernatants to a concentration of 0.4%. The supernatants and the pellet—extracts were then assayed spectrophotometrically for myeloperoxidase activity by determining the rate of decomposition of H$_2$O$_2$ with o-dianisidine as hydrogen donor as described by Renlund, et al. (Renlund, D. G., MacFarlane, J. L., Christensen, R. D., Lynch, R. E., and Rothstein, G., *A Quantitative and sensitive Method for Measurement of Myeloperoxidase*, Clinical Research 28:75A, 1980). Myeloperoxidase activity released into the supernatant was expressed as the percent of the average total activity (pellet plus supernatant).

LTB$_4$ Receptor Binding Assay

Neutrophils (4–6×10$^6$) in 1 ml Hanks' balanced salt solution containing 10 mM HEPES buffer (HBSS), pH 7.4 and 30 μM nordihydroguaiaretic acid were incubated with $0.6 \times 10^{-9}$ M (3H) LTB$_4$ in the presence or absence of test compounds. The incubation was carried out at 0° C. for 45 minutes and terminated by adding 5 ml of ice-cold HBSS followed by rapid filtration of incubation mixture under vacuum through GF/C glass fiber filters. The filters were further washed with 10 ml HBSS and radioactivity was determined. Specific binding was defined as the difference between total binding and nonspecific binding which was not displaced by $10^{-7}$M unlabeled LTB$_4$. All data refer to specific binding.

Modified Boyden Chamber Chemotaxis

Human neutrophils were isolated from citrated peripheral blood using standard techniques of dextran sedimentation, followed by centrifugation on Histopaque ® sterile solution (Sigma) or Ficoll-paque ® (Pharmacia) and hypotonic lysis of erythrocytes. A final cell suspension of $3.4 \times 10^6$ neutrophils/ml of HEPES-buffered Hanks balanced salt solution (HBSS, pH 7.3) was added to the upper well (0.8 ml) of a modified Boyden chamber (blind well). The lower well (0.2 ml), separated by a polycarbonate membrane (Nuleopore Corp.), contained HBSS or $3 \times 10^{-8}$M LTB$_4$ in the presence of absence of test compound. Following a 90 minute incubation at 37° C. in 5% CO$_2$-95% air, cells from the lower well were lysed and nuclei counted in a Model S-Plus-IV Coulter Counter. Percent inhibition was calculated from cell counts corrected for random migration by subtracting the mean of the HBSS control.

The compounds of this invention can be administered in a number of dosage forms. A preferred method of delivery would be oral or in such a manner so as to localize the action of the inhibitor. In an inflammatory condition such as rheumatoid arthritis the compounds could be injected directly into the affected joint. The compounds could also be administered in oral unit dosage forms such as tablets, capsules, pills, powders or granules. They may be introduced intraperitoneally, subcutaneously, or intramuscularly using forms known to the pharmaceutical art. Topical application in the form of salves and ointments are useful for treating psoriasis. Regardless of the route of administration selected, the compounds are formulated into pharmaceutically acceptable dosage forms by conventional methods known to the pharmaceutical art.

Results for representative compounds of the invention are shown in Table 1.

Data are expressed as potency relative to compound 1 in Scheme L, 7-[3,(4-acetyl-3-methoxy-2-propylphenoxy) propoxy]-3,4-dihydro-8-propyl-2H-1-benzopyran-2-carboxylic acid, which is disclosed generally in U.S. Pat. No. 4,889,871.

TABLE 1

Relative Potency Values for LTB$_4$ Antagonists

| Compound | | LTB$_4$ Receptor Binding | Chemotaxis | Degranulation |
|---|---|---|---|---|
| R | R$_1$ | | | |
| Propyl | —C(O)NHSO$_2$Ph | 1.35 | 1.3 | |
| 2-Propenyl | tetrazole (H-N-N/N=N-Y) | 0.8 | 9 | 38 |
| Cyclopropylmethyl | tetrazole (H-N-N/N=N-Y) | 2 | 22.5 | 75 |
| Propyl (Compound 1) | —CO$_2$H | 1.0 ($3 \times 10^{-7}$M) | 1.0 ($1.8 \times 10^{-6}$M) | 1.0 ($1.5 \times 10^{-6}$M) |

Data are expressed as potency relative to a known LTB$_4$ antagonist, compound 1 in Example 1, defined as 1.0. Values in parenthesis refer to IC$_{50}$ values for compound 1. IC$_{50}$ is the effective concentration needed to cause 50% inhibition.

The compounds of this invention can be administered in a number of dosage forms. A preferred method of delivery would be oral or in such a manner as to localize the action of the antagonist. In an inflammatory condition such as rheumatoid arthritis, the compounds could be injected directly into the affected joint. The compounds could also be administered in oral unit dosage forms such as tablets, capsules, pills, powders or granules. They may be introduced intraperitoneally, subcutaneously, or intramuscularly using forms known to the pharmaceutical art. Topical application in the form of salves and art. Topical application in the form of salves and ointments is useful for treating psoriasis. Regardless of the route of administration selected, the compounds are formulated into pharmaceutically acceptable dosage forms by conventional methods known to the pharmaceutical art.

In general, a unit dosage of a compound of the invention would contain from about 50 mg to about 500 mg of the active ingredient with from about 70 mg to about 300 mg preferred.

An effective but non-toxic quantity of the compound is employed in treatment. The dosage regimen for antagonism of LTB$_4$ by the compounds of this invention is selected in accordance with a variety of factors including the type, age, weight, sex, and medical condition of the mammal, the particular disease and its severity, the route of administration and the particular compound employed. An ordinarily skilled physician or veterinarian will readily determine and prescribe the effective amount of the compound to prevent or arrest the progress of the condition. In so proceeding, the physician or veterinarian could employ or use relatively low dosages at first, subsequently increasing the dose until a maximum response is obtained. Generally, a dosage range of 1 to 25 mg/kg of body weight is administered to patients in need of treatment for inflammatory conditions.

What is claimed is:

1. A compound of the formula

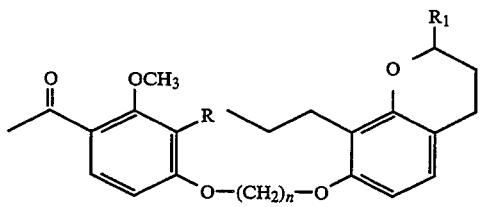

and the stereoisomers and pharmaceutically acceptable salts thereof, wherein R represents lower alkyl of 1 to 6 carbon atoms, lower alkenyl of 2 to 6 carbon atoms, or —(CH$_2$)m R$_3$ wherein R$_3$ represents cycloalkyl of 3 to 5 carbon atoms and m is 1, 2 or 3;

R$_1$ is —CONH$_2$ or

wherein R$_2$ is lower alkyl, phenyl, unsubstituted or substituted with lower alkyl;

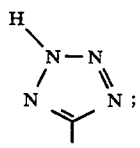

and n is an integer from 2 to 5.

2. A compound of claim 1 wherein R is lower alkyl of 1 to 6 carbon atoms or —(CH$_2$)mR$_3$ R$_1$ is —CONH$_2$ or

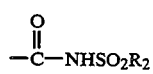

wherein R$_2$ is phenyl unsubstituted or substituted with lower alkyl; or

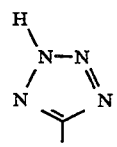

and n is 3, 4 or 5.

3. A compound of claim 2 wherein R is propyl, 2-propenyl or cyclopropylmethyl; R$_1$ is —CONH$_2$, —CONHSO$_2$R$_2$, or

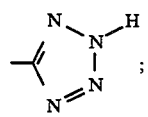

R$_2$ is phenyl; and n is 3, 4 or 5.

4. A compound of claim 3 wherein R is 2-propenyl; R$_1$ is

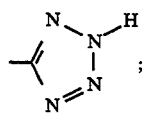

and n is 3.

5. A compound of claim 3 wherein R is cyclopropylmethyl; R$_1$ is

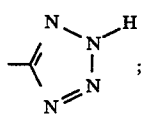

and n is 3.

6. A compound of claim 3 wherein R is propyl; R$_1$ is

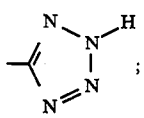

and n is 3.

7. A compound of claim 3 wherein R is propyl; R$_1$ is

wherein R$_2$ is phenyl; and n is 3.

8. A compound of claim 3 wherein R is cyclopropyl methyl; R$_1$ is —CONH$_2$; and n is 3.

9. A compound of claim 3 wherein R is 2-propenyl; R$_1$ is —CONH$_2$; and n is 3.

10. A pharmaceutical composition for treating inflammatory diseases comprising a therapeutically effective amount of a compound of the formula

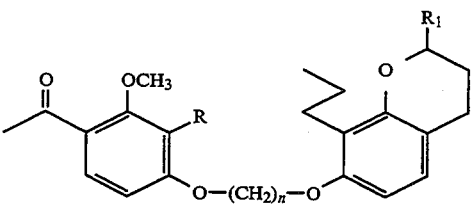

and the stereoisomers and pharmaceutically acceptable salts thereof, wherein R represents lower alkyl of 1 to 6 carbon atoms, lower alkenyl of 2 to 6 carbon atoms, or —(CH$_2$)m R$_3$ wherein R$_3$ represents cycloalkyl of 3 to 5 carbon atoms and m is 1, 2 or 3;

R$_1$ is —CONH$_2$ or $$-\overset{O}{\underset{\|}{C}}-NHSO_2R_2$$

wherein $R_2$ is lower alkyl, phenyl, unsubstituted or substituted with lower alkyl; or

[triazole structure]

and n is an integer from 2 to 5, and a pharmaceutically acceptable carrier.

11. The pharmaceutical composition of claim 10 wherein R is lower alkyl of 1 to 6 carbon atoms or —(CH$_2$)m R$_3$ wherein R$_3$ represents cycloalkyl of 3 to 5 carbon atoms and m is 1, 2 or 3; and $R_1$ is —CONH$_2$ or $$-\overset{O}{\underset{\|}{C}}-NHSO_2R_2$$

wherein $R_2$ is phenyl, unsubstituted or substituted with lower alkyl; or

[triazole structure]

and n is 3, 4 or 5.

12. The pharmaceutical composition of claim 11 wherein R is proyl, 2-propenyl or cyclopropylmethyl; $R_1$ is $$-\overset{O}{\underset{\|}{C}}NHSO_2R_2 \text{ or } \text{[triazole]}$$

$R_2$ is phenyl and n is 3, 4 or 5.

13. The pharmaceutical composition of claim 12 wherein R is 2-propenyl; $R_1$ is

[triazole structure]

and n is 3.

14. The pharmaceutical composition of claim 12 wherein R is cyclopropylmethyl; $R_1$ is

[triazole structure]

and n is 3.

15. The pharmaceutical composition of claim 12 wherein R is propyl; $R_1$ is

[triazole structure]

and n is 3.

16. The pharmaceutical composition of claim 12 wherein R is propyl; $R_1$ is $$-\overset{O}{\underset{\|}{C}}NHSO_2 R_2$$

wherein $R_2$ is phenyl; and n is 3.

17. The pharmaceutical composition of claim 12 wherein R is cyclopropyl methyl; $R_1$ is —CONH$_2$; and n is 3.

18. The pharmaceutical composition of claim 12 wherein R is 2-propenyl; $R_1$ is —CONH$_2$, and n is 3.

19. A method of treating leukotriene B$_4$ mediated diseases comprising administering to a mammal in need of such treatment a therapeutically effective amount of a compound of the formula

[Structure I: acetyl-methoxyphenyl-R-O-(CH$_2$)$_n$-O-chroman with $R_1$]

the stereoisomers and pharmaceutically acceptable salts thereof, wherein R represents lower alkyl of 1 to 6 carbon atoms, lower alkenyl of 2 to 6 carbon atoms, or —(CH$_2$)m R$_3$ wherein R$_3$ represents cycloalkyl of 3 to 5 carbon atoms and m is 1, 2 or 3;

$R_1$ is —CONH$_2$ or $$-\overset{O}{\underset{\|}{C}}-NHSO_2R_2$$

wherein $R_2$ is lower alkyl, phenyl, unsubstituted or substituted with lower alkyl; or

[triazole structure]

and n is an integer from 3, 4 to 5.

20. The method of claim 19 wherein R is lower alkyl of 1 to 6 carbon atoms or —(CH$_2$)m R$_3$ R$_1$ is —CONH$_2$ or $$-\overset{O}{\underset{\|}{C}}-NHSO_2R_2$$

wherein $R_2$ is phenyl, unsubstituted or substituted with lower alkyl; or

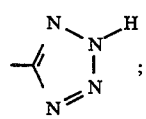

and n is 3, 4 or 5.

21. A method of treating inflammatory diseases comprising administering to a mammal in need of such treatment a therapeutically effective amount of a compound of the formula

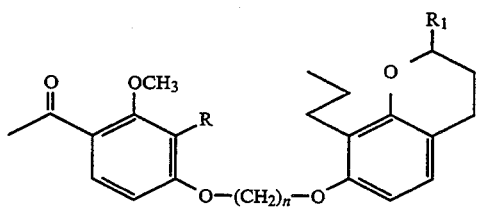

the stereoisomers and pharmaceutically acceptable salts thereof, wherein R represents lower alkyl of 1 to 6 carbon atoms, lower alkenyl of 2 to 6 carbon atoms, or (CH$_2$)m R$_3$;

R$_1$ is —CONH$_2$ or

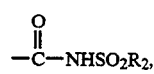

wherein R$_2$ is lower alkyl, phenyl, unsubstituted or substituted with lower alkyl; or

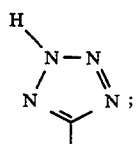

and n is an integer from 2 to 5.

22. The method of claim 21 wherein R is lower alkyl of 1 to 6 carbon atoms or —(CH$_2$)m R$_3$;

R$_1$ is —CONH$_2$ or

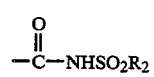

wherein R$_2$ is phenyl unsubstituted or substituted with lower alkyl; or

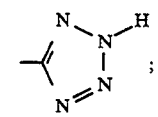

and n is 3, 4 or 5.

23. The method of claim 22 wherein R is propyl, 2-propenyl or cyclopropylmethyl; R$_1$ is

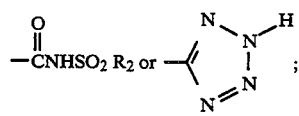

R$_2$ is phenyl; and n is 3.

24. The method of claim 22 wherein R is 2-propenyl; R$_1$ is

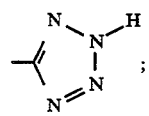

and n is 3.

25. The method of claim 22 wherein R is cyclopropylmethyl; R$_1$ is

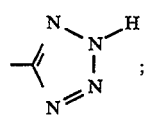

and n is 3.

26. The method of claim 22 wherein R is propyl; R$_1$ is propyl; R$_1$ is;

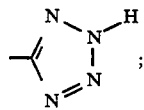

and n is 3.

27. The method of claim 22 wherein R is propyl; R$_1$ is

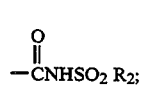

R$_2$ is phenyl; and n is 3.

28. The method of claim 22 wherein R is cyclopropyl methyl; R is —CONH$_2$; and n is 3.

29. The method of claim 22 wherein R is 2-propenyl; R$_1$ is —CONH$_2$; and n is 3.

* * * * *

UNITED STATES PATENT AND TRADEMARK OFFICE
CERTIFICATE OF CORRECTION

PATENT NO. : 5,380,740                     Page 1 of 2
DATED      : January 10, 1995
INVENTOR(S): Djuric, et al.

It is certified that error appears in the above-indentified patent and that said Letters Patent is hereby corrected as shown below:

Column 1, line 38, reading "treating" should read -- in treating --.

Column 2, line 32, reading "pharmaceuticalIF" should read -- pharmaceutically --.

Column 5, line 28, reading "4C ml" should read -- 40 ml --.

Column 12, line 15, reading "*Stand,*" should read -- *Scand.* --.

Column 12, line 60, reading "*sensitive*" should read -- *Sensitive* --.

Column 14, line 7, reading "Scheme L," should read -- Scheme 1 --.

Column 14, line 51, delete the sentence "Topical application in the form of salves and art."

Column 15, line 36 (Claim 1) after "lower alkyl;" insert -- or --.

Column 15, line 47 (Claim 2) between "$R_3$" and "$R_1$" insert -- ; --.

Column 18, line 60 (Claim 20), between "$R_3$" and "$R_1$" insert -- ; --.

UNITED STATES PATENT AND TRADEMARK OFFICE
CERTIFICATE OF CORRECTION

PATENT NO. : 5,380,740
DATED : January 10, 1995
INVENTOR(S) : Djuric, et al.

It is certified that error appears in the above-indentified patent and that said Letters Patent is hereby corrected as shown below:

Column 19, line 29 (Claim 21), between "$R^3$" and ";" insert -- wherein $R_3$ represents cycloalkyl of 3 to 5 carbon atoms and m is 1, 2 or 3 --.

Column 20, line 38, after "$R_1$ is" delete ";".

Signed and Sealed this

Thirtieth Day of January, 1996

Attest:

BRUCE LEHMAN

Attesting Officer

Commissioner of Patents and Trademarks